United States Patent [19]

Tihon

[11] Patent Number: 5,562,622
[45] Date of Patent: Oct. 8, 1996

[54] SELF-CLEANSING BLADDER DRAINAGE DEVICE

[75] Inventor: Claude Tihon, Eden Prairie, Minn.

[73] Assignee: ContiMed, Inc., Eden Prairie, Minn.

[21] Appl. No.: 407,297

[22] Filed: Mar. 20, 1995

[51] Int. Cl.$^6$ .................................................. A61M 29/00
[52] U.S. Cl. ........................ 604/105; 604/329; 604/349; 128/761
[58] Field of Search ..................................... 604/104–107, 604/54, 93, 245, 329, 349, 350, 352; 606/198; 128/761, 766

[56] References Cited

U.S. PATENT DOCUMENTS

| | | |
|---|---|---|
| 2,450,217 | 9/1948 | Alcorn . |
| 3,260,258 | 7/1966 | Berman . |
| 3,490,456 | 1/1970 | Kortum .................................... 604/106 |
| 3,769,981 | 11/1973 | McWhorter . |
| 3,774,591 | 11/1973 | Corbin .................................... 128/761 |
| 3,811,450 | 5/1974 | Lord . |
| 3,815,608 | 6/1974 | Spinosa .................................. 604/105 |
| 3,821,956 | 7/1974 | Gordhamer ............................. 604/104 |
| 4,398,910 | 8/1983 | Blake ...................................... 604/93 |
| 4,710,169 | 12/1987 | Christopher ............................ 604/349 |
| 4,723,946 | 2/1988 | Kay . |
| 4,738,667 | 4/1988 | Galloway . |

Primary Examiner—Randall L. Green
Assistant Examiner—Chalin Smith
Attorney, Agent, or Firm—Haugen and Nikolai, P.A.

[57] ABSTRACT

An urethral drain having deep external drainage channels, a low-profiled bladder retention segment, and a reversibly detachable collection segment, facilitates the draining of urine and fluids from the bladder. The low-profiled retention means minimizes bladder irritations and the deep external channels reduce the occurrence of infections. Incorporation of a reduced diameter smooth segment on the catheter, proximate the location of the external urethral sphincter allows the patient to void normally and at will. The drain can be worn concealed within the urethra. Flushing action from normal voiding washes out particulate matters in the urethra and the concealed drain further minimizes contamination. Together, these features improve quality of life for patients needing catheterization.

17 Claims, 12 Drawing Sheets

SELF-CLEANSING BLADDER DRAINAGE DEVICE

BACKGROUND OF THE INVENTION

I. Field of the Invention

This invention relates generally to body fluid drainage devices, and more particularly to a urinary drain having improved performance characteristics.

II. Discussion of the Prior Art

Urethral catheters, such as the Foley catheter, now used for bladder drainage are essentially elongated tubular structures placed in the urethra for draining urine through the lumen thereof. Near the distal end of the tube is an inflatable balloon which, when inflated while in the bladder, allows the catheter to be held in place. Its proximal end has a drainage port as well as a balloon inflation port. The proximal end of the catheter protrudes beyond the urethral orifice and can be attached to a bag receptacle for the collection of the near constantly dripping urine from the bladder. The collection bag is either attached to the patient's leg when the patient is ambulatory, or to the side of the bed during bed rest. At times, a plug is used in place of the bag to stop the leakage of urine from the catheter tip.

When Foley catheters or the like are used, patients are not able to void when they want to. Rather, urine is continuously drained from the bladder through the elongated tube and into the collection bag. Ambulatory patients are therefore obligated to have the leg bag attached to their leg, and this poses a source of great inconvenience, unsightliness and problems affecting their quality of life. Due to the fact that urine is continuously being drained from the bladder, the bladder is continuously near empty. The dome of the bladder, therefore, rests continuously on the water-filled bulging balloon retention part of the Foley catheter, causing tissue compression, irritation and erosion related adverse side effect problems. Furthermore, increased urinary tract infection is common with patients using such catheters, especially when used on a chronic basis. Though the casual factors have not been precisely identified, length of time of catheterization has been associated with an increased frequency and severity of urinary tract infection, presumably due to the migration of bacteria up the urethral tract. Frequently, yellow encrusted and mucoid proteinaceous depositions containing bacteria are found on the surfaces of the catheter with much higher concentration on the inner lumen surfaces. The mandated usage of urine receptacles causes additional associated stigma of soiled clothing, furniture and odor.

SUMMARY OF THE INVENTION

The present invention provides a solution to increase the quality of life for patients who require drainage catheters by solving compression and irritation related problems, giving patients an option to carry on their daily lives more normally and reduce incidence of the common urinary tract infections. The invention comprises a bladder drainage device having at least one deep, open fluid-drainage channels and a low profiled bladder retention means at its distal end. In addition, it can contain a smooth segment, preferably narrowed, in the area of the external urethral sphincter. Urine drains from the bladder via the open surface channels. The narrowed smooth segment permits the external urethral sphincter to function normally to shut off the leakage of urine from the bladder to the lower portion of the urethra. The drainage channels reappear below the external sphincter. When the sphincter opens, urine and fluid will flow past the relaxed sphincter area at the smooth, narrowed drain region, and down to the deep surface drainage channels below. Unlike the situation with the Foley type catheter, where urine is continuously drained in a leaking fashion from the bladder through an internal lumen, the present configuration of the invention allows urine to be stored in the bladder until voided in mass, much as in a normal manner, when the patient is ready to do so. Due to this natural and daily multiple automatic flushing action in the urethra and channel walls by a rushing of the bolus or urine, the bladder drain of the present invention is self-cleansing without any added external pressurized flushing equipment means, such as that described in U.S. Pat. No. 4,723,946, or any added steps for the patient.

The device of the present invention, without the smooth segment, can be worn by patients in cases where constant urine drainage is required or unavoidable. Thus, the drain will have the benefits of the lower profile retention means for reduced bladder irritability, and the deep external drainage channel(s) causing urine flow to be in contact with the urethral wall to minimize colonization of bacteria and other contaminants within a lumen, thus lower possibility of infections.

The presence of the narrow, smooth segment at the site of the external urethral sphincter region allows the natural constriction of the external urethral sphincter to terminate the flow of fluid to the distal bulbous and penile urethra as the sphincter normally functions. The patient is, therefore, able to control his own voiding frequency. This permits the drain device to be worn by ambulatory patients without the necessity of an external urine drainage collection leg bag.

Patients suffering from urinary incontinence have differing degrees of contractibility of the external urinary sphincter, depending upon age and other factors. By providing a smooth surface section that can be repositioned along the length of the externally grooved drain member and which can be selected for its outer diameter, a variety of patients can be accommodated.

The distal end of the drain device located within the bladder contains a retention means for retaining it at the bladder neck. This preferably a coiled section of the flexible, deep open channeled drainage device, which is initially straightened for insertion in the urethra by a straightening stylet placed in a central lumen of the drain device. Removing the wire after drain placement restores the curl. Due to the fact that the low profile retention means is an extension of the drainage segment, no balloon is needed, nor is there a necessity for a perpendicular, upward-protruding tubing with lateral openings for the passage of urine. The retention means is spaced apart form the smooth narrowed section a distance to assure drainage within the prostatic urethra. Before exiting the urethra, the deep channels are replaced by a traditional tubular structure, the collection segment, which proceeds to exit the urethra. This collection segment collects fluid from the deep external channel(s) above, transports it beyond the meatus of the penis, and permits the attachment of a urine drainage collection bag or a plug at the proximal end. The tubular collection segment can be detached from the channeled main drain body, thus leaving the entire drain device concealed inside the urethra. This further insures minimal infection from outside contamination, and avoids the aesthetically displeasing and uncomfortable presence of an external device. Thus, the object of this invention is to greatly increase the quality of life for patients who require bladder drainage catheters.

BRIEF DESCRIPTION OF THE DRAWINGS

The foregoing features and advantages of the invention will become apparent to those skilled in the art from the following detailed description of the present invention, in which numerals in the several view refer to corresponding parts.

FIG. 1A is a partial view of the bladder drain of FIG. 1, but with an alternative anchoring structure;

DETAILED DESCRIPTION OF THE PREFERRED EMBODIMENT

Figure 1:
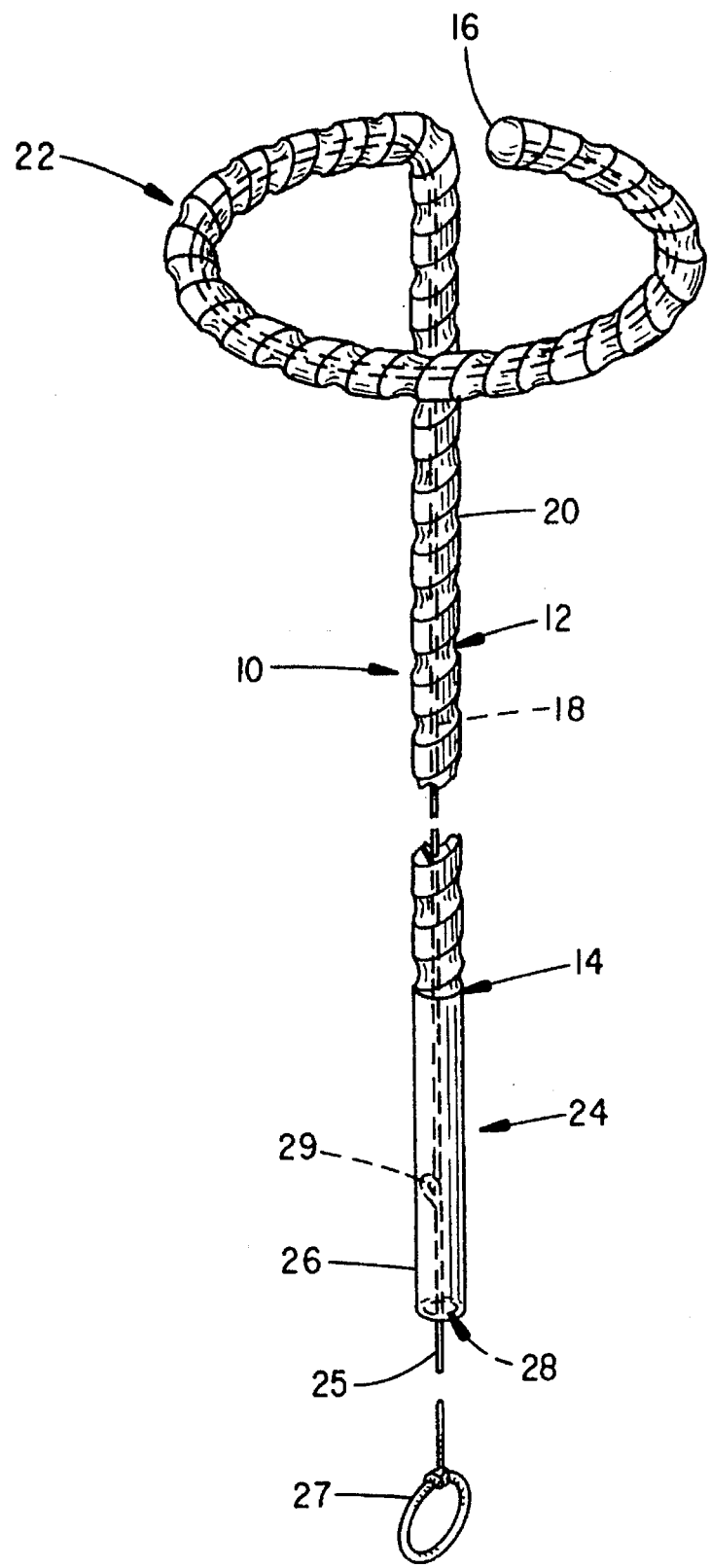
FIG. 1 is an elevational view of a bladder drain in accordance with a first embodiment of the invention.
Figure 1:
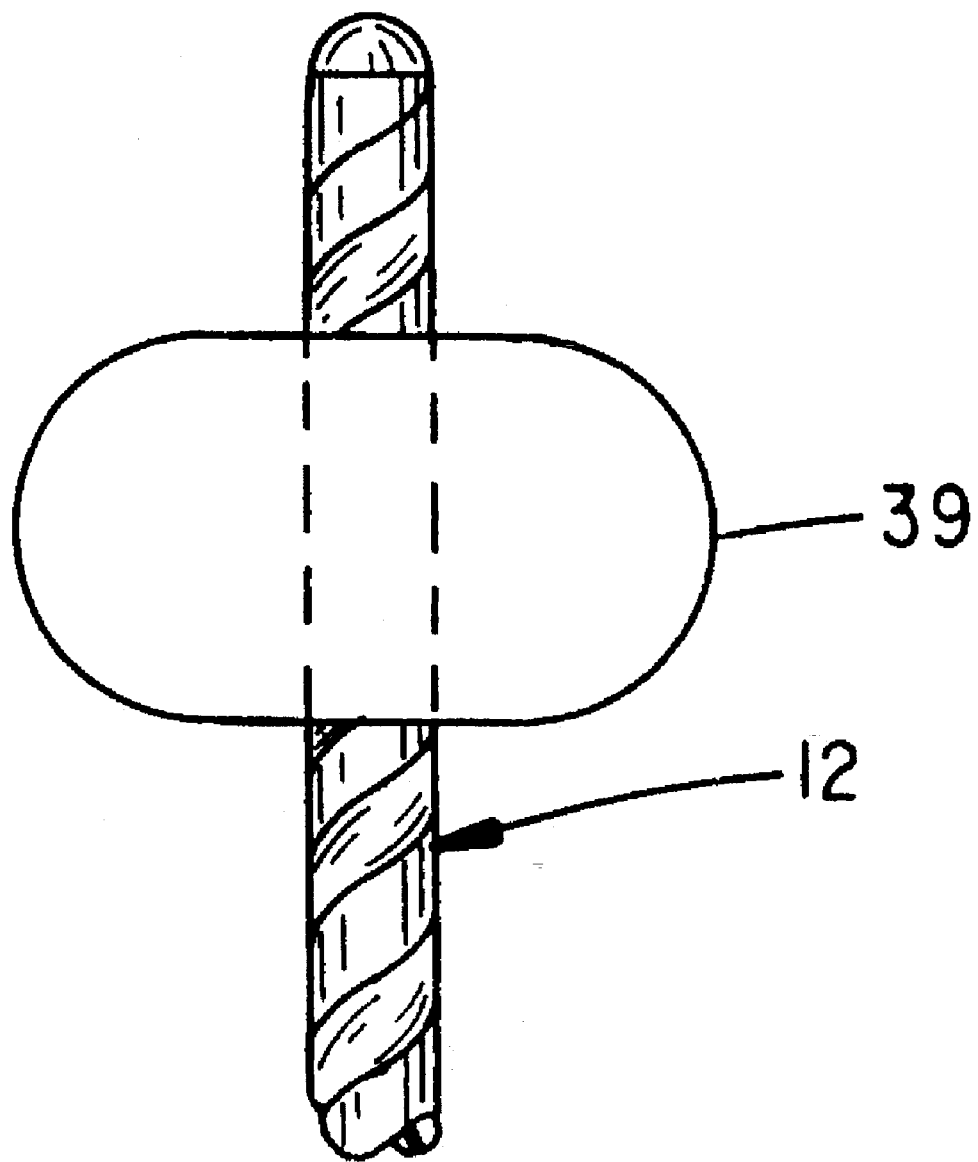

Referring first to FIG. 1, there is shown a perspective view of a bladder drainage device in accordance with a first embodiment of the invention. It is indicated generally by numeral 10 and is seen to comprise an elongated, flexible tubular member 12 having a proximal end 14 and a distal end 16 and with a stylet receiving lumen 18 extending longitudinally toward but just short of the distal end 16. Thus, the distal end 16 covers the stylet lumen precluding the flow of body fluids therethrough when the drainage device 10 of the present invention is in place within the urethra of a patient.

With continued reference to FIG. 1, the body member 12 of the drainage device 10 is shown as including at least one spiral groove 20 formed in the surface thereof as it extends substantially the entire distance from the proximal end 14 to the distal end 16. With no limitation intended, for a drain device having an outside dimension of 0.21 inches, the helical groove 20 may have a depth of approximately 0.06 inches. The body member is preferably fabricated from a flexible polymer material, such as silicone, silastic, polyurethane or another thermoplastic elastomer having a durometer shore hardness between about 30 and 95 shore A.

Disposed proximate the distal end of the bladder drain device is a bladder retention segment 22 which comprises a curled end portion which can be straightened by the full insertion of a wire stylet (not shown) through the lumen 18. However, when the stylet is fully withdrawn following insertion of the drain assembly as shown in FIG. 1, the memory property of the plastic comprising the distal end portion of the drainage device 10 allows the preformed distal end, bladder-retaining portion 22 to form a loop or curl as illustrated. Those skilled in the art can appreciate that means other than a controlled memory property are available for creating the curl on the distal end of the drainage device. For example, a short wire segment having a preformed shaped can be embedded into the body of the drain.

Attached to the proximal end of the bladder drain 10 is a fluid collection segment indicated generally by numeral 24. The fluid collection segment 24 may be attached and detached from the drainage segment 12 in a manner that will be described later herein. In its simplest form, the collection segment 24 comprises an elongated plastic tube having an internal lumen extending from the proximal end 14 of the drain segment to an open distal end 28 which forms the drain outlet. The collection segment 24 can accept a drainage bag or a plug not shown.

To facilitate removal of the drain, a monofilament nylon line 25 is fixedly secured to the proximal end 14 of the drain 12 and extends beyond the proximal end 28 of the collection segment 24 and out the urethral opening in the penis. By grasping the monofilament line 25 by the loop 27 and pulling on the line, the memory property of the fixation member 22 is overcome and the drain can be readily pulled through the urethra and out the end of the penis. If desired, the line 25 may terminate short of the proximal end 28 of the collection segment 24 and in that event, an instrument having a hook on it may be passed up the lumen of the collection segment 24 to grasp a loop 29 tied in the line. By now pulling on the instrument, the drain member 12 can again be removed.

Figure 2:
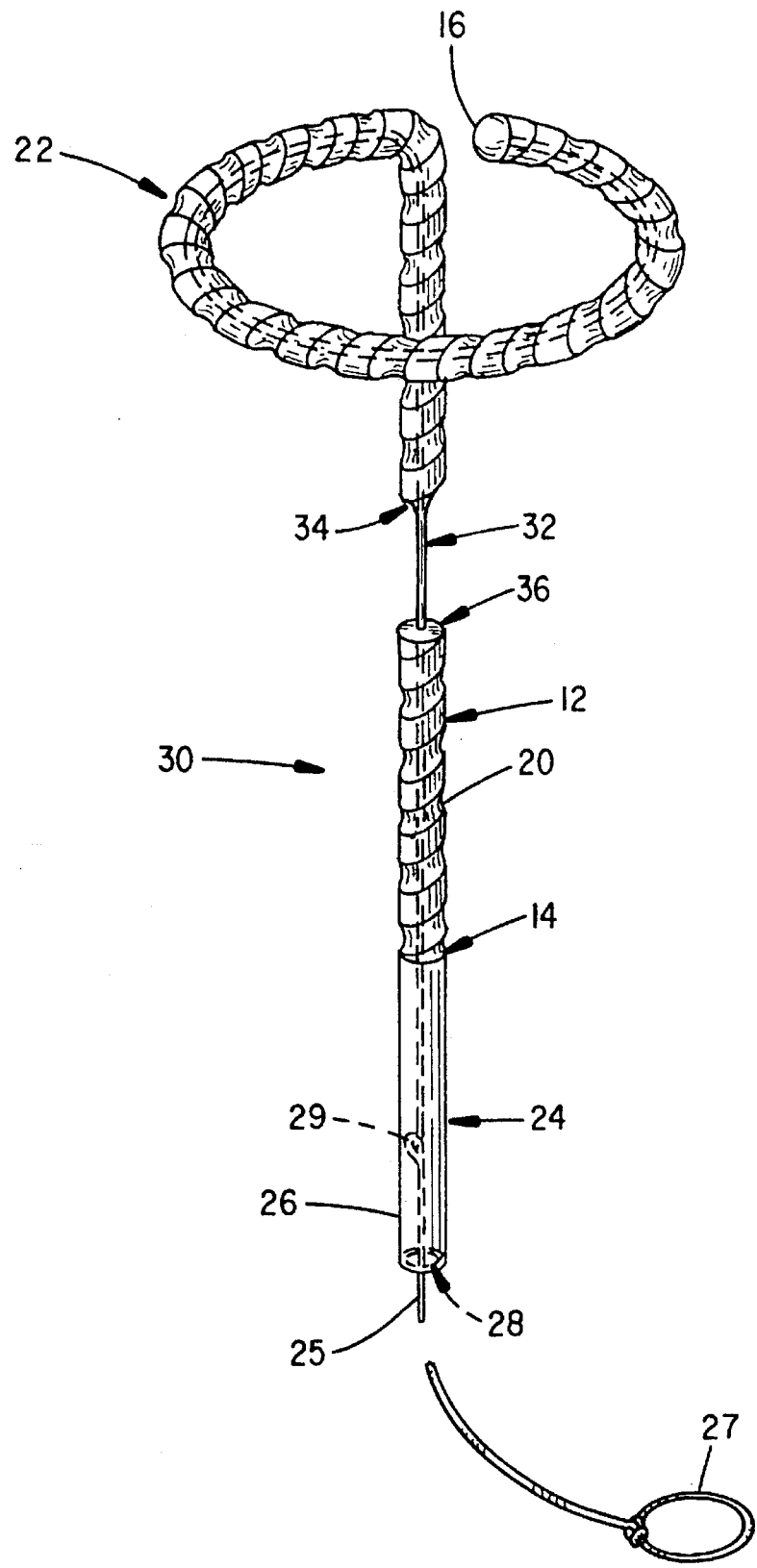
FIG. 2 is an elevational view of an alternative embodiment of the bladder drain in accordance with the invention.

An alternative embodiment of the invention is depicted in FIG. 2. The assembly of FIG. 2 is similar in most respects to the embodiment of FIG. 1 except that in the device 30 of FIG. 2, the drainage member 12 includes a narrowed and smooth (non-grooved) urethral external sphincter segment 32. At the distal end of the segment 32 is a tapered shoulder 34 and at the proximal end is a more squared shoulder 36. The length of the segment 32 is preferably in the range of from 0.5 cm to 3.5 cm.

Figure 3:
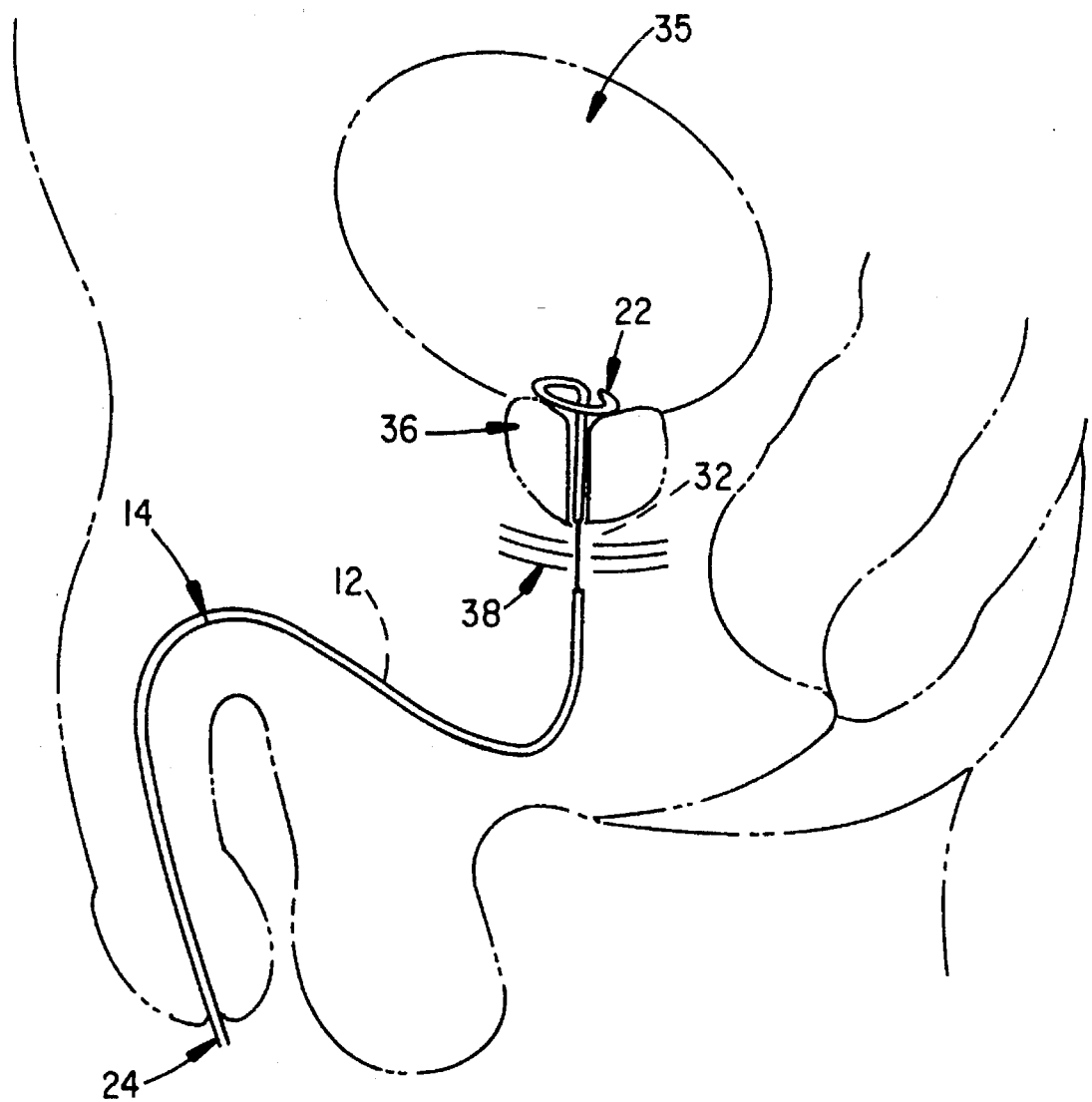
FIG. 3 is a view illustrating the embodiment of FIG. 2 inserted in the male urethra.

Referring next to FIG. 3, it shows the bladder drain device of the embodiment of FIG. 2 disposed in the male urethra. The bladder retention portion 22 is located proximate the neck of the bladder 35 and with the installation stylet (not shown) fully removed, the bladder retention portion assumes its wide loop configuration, thereby holding the drainage device in place. The portion of the drainage device 12 located above the tapered shoulder 34 is dimensioned to traverse the prostate 36 and with the zone 32 of reduced diameter extending through the external urethral sphincter 38.

The circular curl 22 comprising the retention element is essentially perpendicular to the axial length of the drain and does not protrude appreciably above the base of the bladder. This low profile distinguishes the present invention from the common Foley catheter, which is retained by means of a liquid filled balloon, as well as from the device shown in U.S. Pat. No. 4,738,667 to Galloway. The removal of a straightening stylet, as compared to the removal of an outer shield in the Galloway device, serves to minimize any irritation to the urethral wall of the patient. The use an internal straightening wire, as contrasted to a design utilizing an external straightening sleeve, also allows the existence of deeper drainage channels for a given outer diameter of the drain itself. While the bladder retention segment is depicted as a spiral or curl at the distal end of the body member 12 comprising the drain, it can be appreciated that an inflatable balloon adhered to the exterior of the tubular body 12 and communicating through a port bridged by the balloon leading to an inflation lumen may be employed to anchor the drain in a fashion similar to what is conventionally used with a Foley catheter. Such as an arrangement is shown in FIG. 1A, with the silastic balloon identified by numeral 39.

With the embodiment of FIG. 2 in place, as illustrated in FIG. 3, there will be a continuous flow of urine from the bladder 34 through the channel 20 formed in the exterior wall of the drain segment 12 with the channel emptying into the lumen of the urine collection tube 24. For patients having a functioning external urethral sphincter 38, the compressional force on the urethra in the zone 32 of the drain will close the urethra against that segment thereby blocking urine flow. When the patient desires to drain his or her bladder, he or she relaxes the external urethral sphincter 38 allowing the contents of the bladder 35 to flow through the channels formed in the wall surface of the drainage device 12 to again empty into the urine collection tube 24 leading to a collection bag (not shown).

Figure 4:
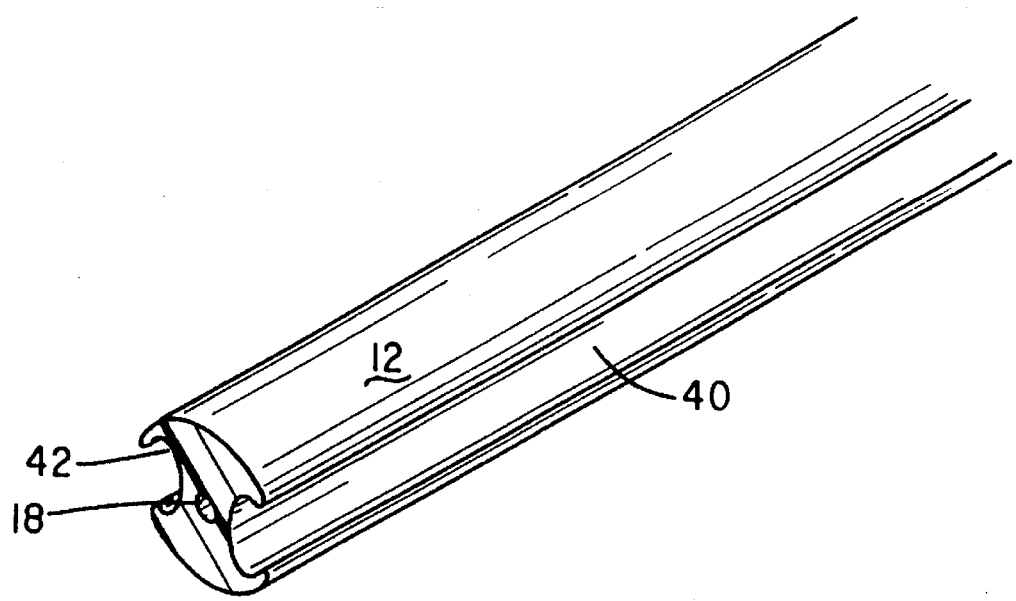
FIG. 4 is a fragmentary, enlarged perspective view of the portion of a bladder drain, illustrating straight surface grooves.
Figure 5:
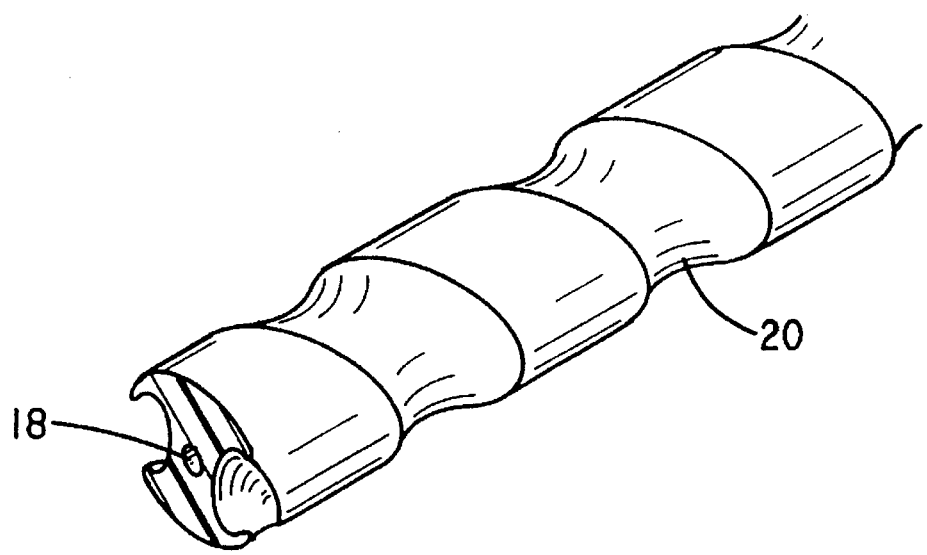
FIG. 5 is a fragmentary, enlarged perspective view of a portion of a bladder drain illustrating spiral surface grooves.

FIGS. 4 through 7 are included to show alternative ways of configuring the drainage segment 12 of the present invention. In FIG. 4, the drainage segment 12 includes two straight longitudinal channels 40 and 42 diametrically opposed from one another and extending substantially the entire length of the drainage segment. Also visible in FIGS. 4 through 7 is the stylet lumen 18. In the embodiment of FIG. 5, the surface grooves, as at 20, form a spiral, as in the embodiments of FIGS. 1 and 2. This spiral pattern may conveniently be formed during the fabrication process by twisting the segment 12 during its extrusion. By controlling the amount of twisting, the pitch of the channels can be controlled.

While linear channels of the type shown in FIG. 4 may be provided in the drainage segment, a spiral channel configuration is preferred in that the lateral projections on the outer surface of the drain will interact with the urethral wall in such a fashion as to retard movement of the drain along the axial length of the urethra, thus minimizing undesired migration thereof. The side walls of the channels are preferably undercut or dished, as at 44 (FIG. 6), to thereby prevent irritation of the urethra, and to inhibit invagination of the urethral wall tissue into the channels.

Figure 6:
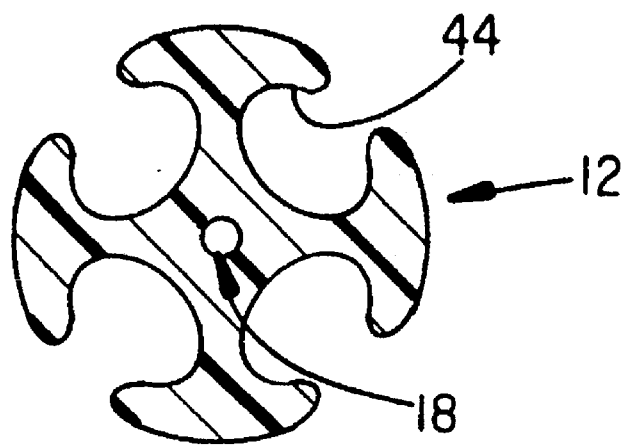
FIG. 6 is an enlarged cross-sectional view of a portion of the body of a bladder drain having four surface grooves extending the length thereof.
Figure 7:
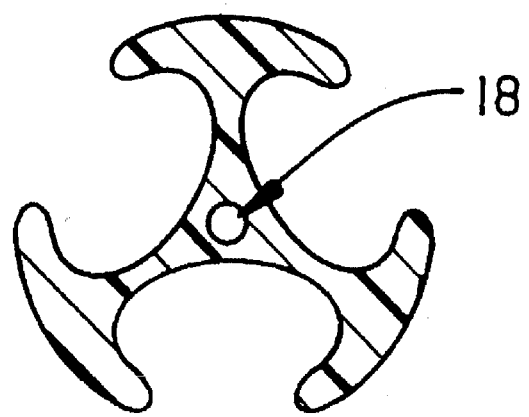
FIG. 7 is an enlarged cross-sectional view through a portion of the body of a bladder drain having three surface grooves extending along the length dimension thereof.

FIGS. 6 and 7, respectively, show cross-sectional views of the drain in which four and three channels, respectively, extend the length thereof.

Figure 8:
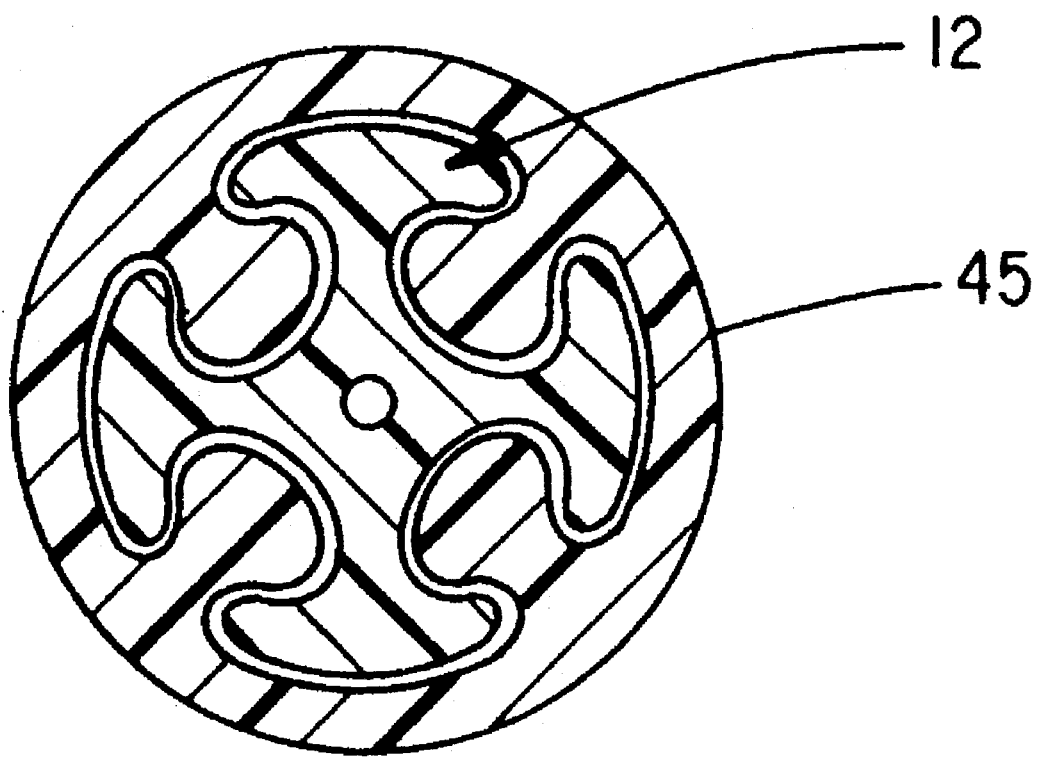
FIG. 8 is an enlarged cross-sectional view through a portion of the body of a bladder drain having a positionable smooth sleeve segment affixed thereto.

Referring to the cross-sectional view of FIG. 8, another way of forming a smooth segment along the length of the drainage member 12 for cooperating with the external urinary sphincter of a given patient is to provide a short length of tubing, as at 45, having an internal lumen whose side walls are complimentary in shape to the exterior surface of the grooved drainage member 12. Thus, the smooth portion of the tube 45 can be longitudinally adjusted to a location along the drain body where the urinary sphincter is located for that patient. Also, the outside diameter of the removable and replaceable smooth tubular segment 45 can be selected to accommodate the particular contractibility of the urinary sphincter of the patient to provide increased continence. It has been determined that an outer diameter falling in the range of from about 0.1 cm to 1.0 cm can accommodate a majority of patients.

It is further contemplated that the smooth tubular member 45 can comprise an inflatable sleeve surrounding the drain member 12. This is deemed to be beneficial in cases of female stress incontinence in that the sleeve can be inflated after placement to a degree effective to preclude leakage between the expandable sleeve and the neck of the bladder.

Figure 9:
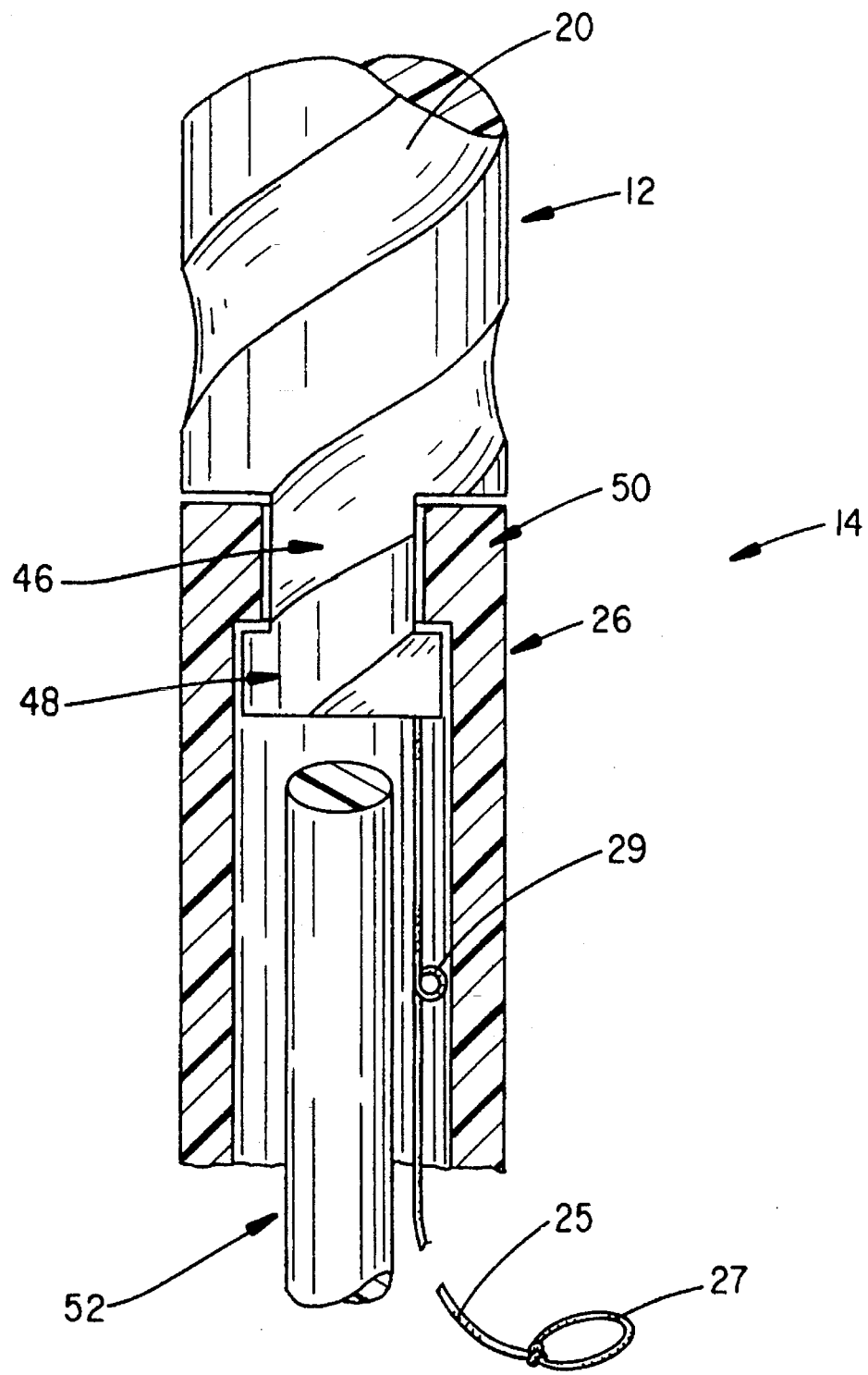
FIG. 9 is a partially sectional, fragmentary view of the embodiment of FIGS. 1 or 2 proximate the junction between the grooved bladder drain element and its associated collection segment.
Figure 9:
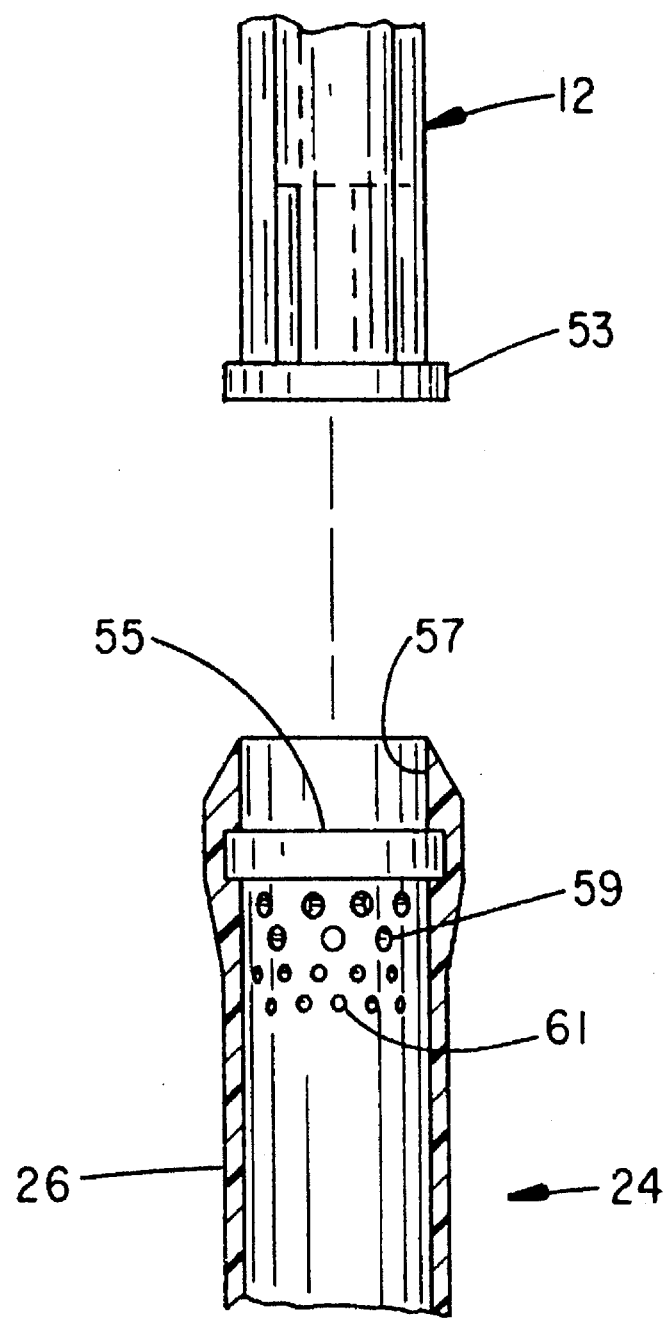
Figure 11:
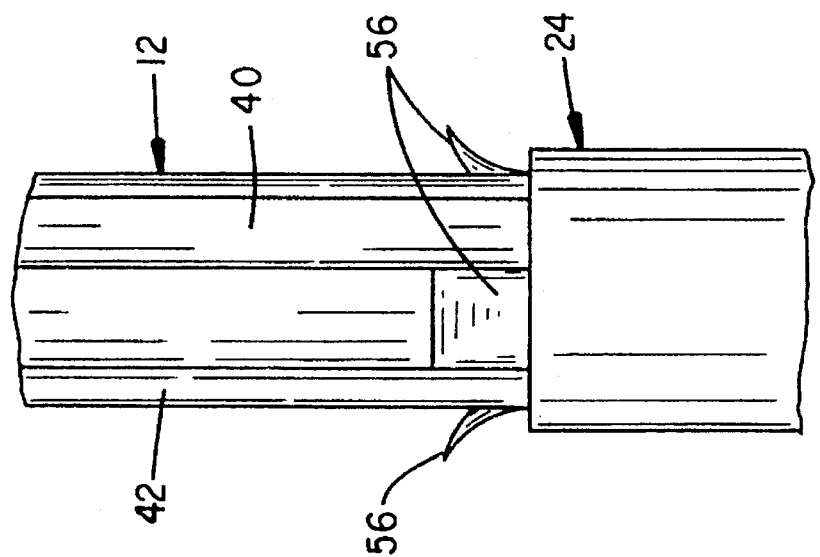
Figure 10:
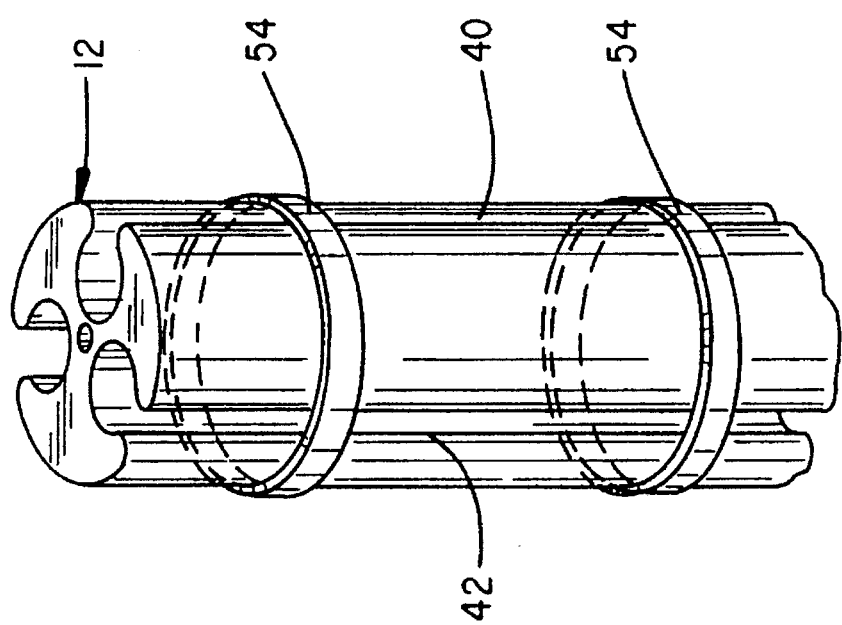
Figure 14:
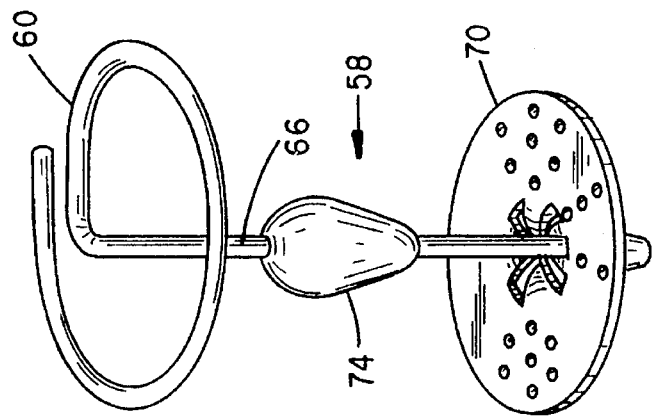
Figure 13:
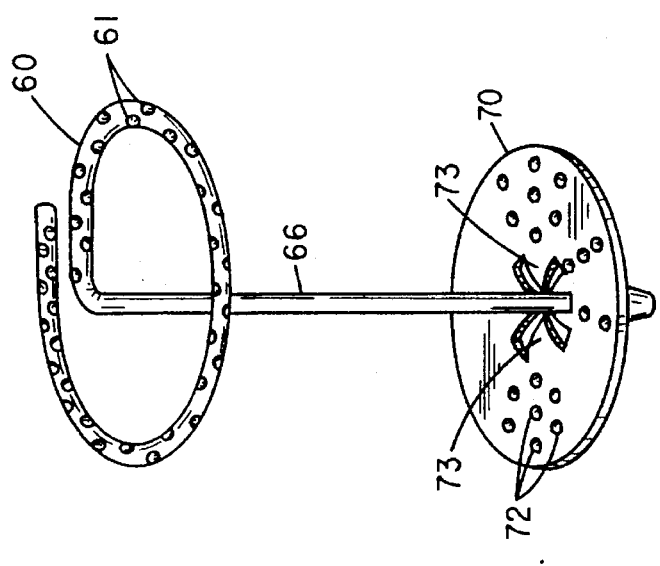
Figure 12:
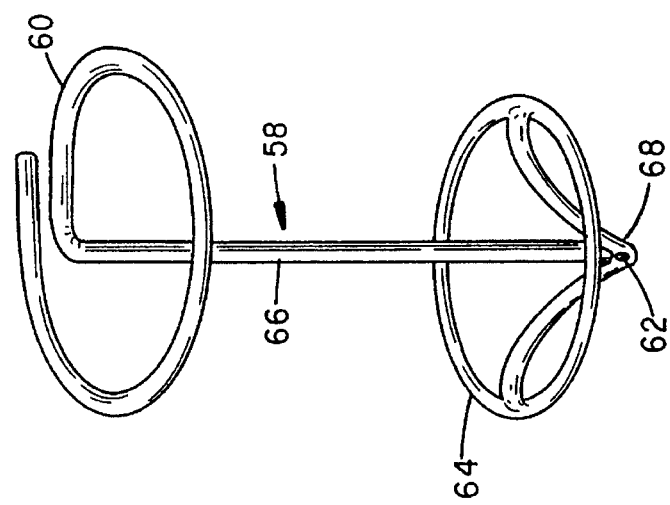
Figure 15:
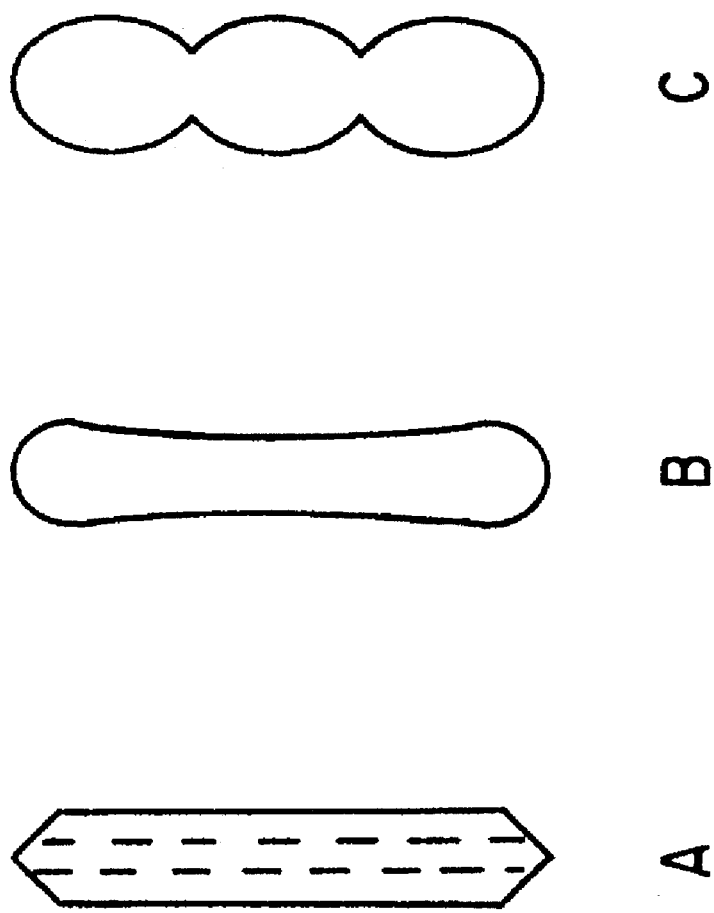

Referring now to FIG. 9, there is shown an enlarged fragmentary, partially sectioned view of the bladder drain showing the manner in which the fluid collection tube 24 is joined to the proximal end of the grooved drainage member 12. The proximal end 14 of the drainage member 12 is provided with a narrowed neck 46 which is followed by an expanded end portion 48. The fluid collection tube 26 has a complimentary profile 50 adapted to snap over the end portion 48 to occupy the narrowed neck 46. Urine passing along the grooves 20 between the internal wall of the urethra and the drain is channeled into the lumen of the collection tube 26 to flow out its proximal end 28, either continuously when the embodiment of FIG. 1 is employed or in a controlled manner when the embodiment of FIGS. 2 or 8 is utilized. Detachment of the flexible plastic collection tube 26 may be accomplished by pulling on the tube 26 in the proximal direction while simultaneously employing a stabilizing push rod 52 to hold the drainage segment 12 in place. After detachment of the collection tube 26, the drain device is entirely contained within the urethral tract.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A flexible, self-cleaning urethral drain for draining of urine and fluid from the bladder through the urethra of a patient comprising:

(a) a flexible, elongated drain body having a distal end, a proximal end and a generally solid core, the drain body having an outer diameter allowing passage through the urethra;

(b) bladder retention means located adjacent to the distal end of the drain body for retaining the drain body in place in the urethra; and (c) the drain body having at least one open fluid drainage channel on an exterior surface thereof of a depth sufficient for draining urine between the exterior surface of the drain body and the urethral wall.

2. The flexible, self-cleaning urethral drain as in claim 1 and further including a tubular collection segment affixed to the proximal end of the drain body, the tubular collection segment having an internal lumen in fluid communication with the at least one channel for receiving urine from the at least one channel of the drain body, the collection segment terminating at a proximal end external to the urethra.

3. A flexible, self-cleaning urethral drain as in claim 1 wherein the drain body includes an integrally formed longitudinal segment of a uniform diameter which is less than the outer diameter of the drain body and located along the drain body to cooperate with the external urethral sphincter in the patient for providing continence when the sphincter is normally contracted, and allowing passage of urine along the at least one channel when the sphincter is relaxed.

4. A flexible, self-cleaning urethral drain as in claim 1 and further including a positionable sleeve member having a smooth exterior surface void of grooves and an interior surface conforming to the exterior surface of the drain body, including the at least one open fluid drainage channel.

5. The flexible, self-cleaning urethral drain as in claim 3 wherein the length of the longitudinal segment is between approximately 0.5 cm to 3.5 cm.

6. The flexible, self-cleaning urethral drain as in claim 4 wherein the positionable sleeve member has a length between approximately 0.5 cm and 3.5 cm.

7. The flexible, self-cleaning urethral drain as in claim 3 wherein the outer diameter of the longitudinal segment is between approximately 0.1 to 1.0 cm.

8. The flexible, self-cleaning urethral drain as in claim 4 wherein the outer diameter of the positionable sleeve is in the range of from 0.3 cm. to 1.0 cm.

9. The flexible, self-cleaning urethral drain as in claim 3 wherein the drain body tapers to the diameter of the longitudinal segment at a distal end of the longitudinal segment.

10. A flexible, self-cleaning urethral drain as in claim 3 wherein a segment of the drain body proximal to the longitudinal segment joins to the longitudinal segment to form a squared shoulder.

11. The flexible, self-cleaning urethral drain as in claim 1 wherein the bladder retention means comprises a curl at the distal end of the flexible drain body.

12. The flexible, self-cleaning urethral drain as in claim 11 wherein the at least one channel extends along at least a portion of said curl.

13. The flexible, self-cleaning urethral drain as in claim 11 wherein the curl has a flat profile and extends perpendicular to a longitudinal axis of the remainder of the drain body.

14. The flexible, self-cleaning urethral drain as in claim 11 wherein the tubular body includes a stylet receiving lumen and the curl is preformed and can be reversibly straightened by inserting a stiffening stylet in the stylet-receiving lumen.

15. The flexible, self-cleaning urethral drain as in claim 1 wherein the bladder retention means comprises an inflatable member.

16. The flexible, self-cleaning urethral drain as in claim 1 wherein the drain body comprises a flexible polymer material selected from the group including silicone, silastic, polyurethane and polyethylene.

17. The flexible, self-cleaning urethral drain as in claim 16 wherein the polymer material has a durometer in the range of from 30 to 95 shore A.

* * * * *

UNITED STATES PATENT AND TRADEMARK OFFICE
CERTIFICATE OF CORRECTION

PATENT NO. : 5,562,622
DATED : October 8, 1996
INVENTOR(S) : Claude Tihon

It is certified that error appears in the above-indentified patent and that said Letters Patent is hereby corrected as shown below:

In the Drawings:
Delete Sheet 10 of 12, Sheet 11 of 12, and Sheet 12 of 12 of the drawings.

Signed and Sealed this

Seventeenth Day of December, 1996

Attest:

BRUCE LEHMAN

*Attesting Officer*    *Commissioner of Patents and Trademarks*